United States Patent [19]

Monö et al.

[11] 4,292,966
[45] Oct. 6, 1981

[54] AEROSOL INHALATION DEVICE

[75] Inventors: Rune G. Monö, Täby; Nils F. E. Morén, Malmö; Kjell I. L. Wetterlin, S. Sandby, all of Sweden

[73] Assignee: Aktiebolaget Draco, Lund, Sweden

[21] Appl. No.: 118,750

[22] Filed: Feb. 5, 1980

[30] Foreign Application Priority Data

Feb. 16, 1979 [SE] Sweden .................. 7901417

[51] Int. Cl.³ ........................................... A61M 11/04
[52] U.S. Cl. .................................. 128/200.23; 222/3; 222/635; 239/288.5; 239/456; 229/175 C; 217/61; 220/252
[58] Field of Search ............... 128/200.14, 200.15, 128/200.16, 200.21, 200.23, 203.15, 203.23, 203.24; 222/3, 635, 634, 631; 239/288.5, 451, 455, 456, 499; 229/175 C; 217/61, 62; 220/252

[56] References Cited

U.S. PATENT DOCUMENTS

| 476,131 | 5/1892 | Cushman | 128/203.24 |
| 3,001,524 | 9/1961 | Maison et al. | 128/200.23 |
| 3,184,115 | 5/1965 | Meshberg | 128/200.23 X |
| 3,236,458 | 2/1966 | Ramis | 128/200.23 X |
| 3,897,779 | 8/1975 | Hansen | 128/200.23 |

Primary Examiner—Henry J. Recla
Attorney, Agent, or Firm—Brumbaugh, Graves, Donohue & Raymond

[57] ABSTRACT

An aerosol inhalation device comprising an elongated chamber, an outer chamber part of which has an outlet opening and is telescopically displaceable over an inner chamber part which is connectable to an aerosol dispenser and provided with a flexible tongue which on telescoping the device together closes the outlet opening.

2 Claims, 4 Drawing Figures

AEROSOL INHALATION DEVICE

DESCRIPTION

TECHNICAL FIELD

The present invention is related to a device allowing an improved and simplified inhalation of aerosols, especially pharmaceuticals in aerosol form.

BACKGROUND ART

Therapeutically active substances may be administered by inhalation to the lungs of a patient for producing a local effect therein. Thereby a rapid onset of the effect is obtained using a low dosage of the substance, and systemic side-effects are reduced. Pressurized containers, in which the active substance is dissolved or suspended in a propellant such as a chlorofluorocarbon, are often used.

From such a container a dosage is released via a valve system and inhaled through a mouthpiece. On release of the dosage the particles formed have a high velocity. Furthermore the aerosol droplets generated in the orifice of the mouthpiece are large as they contain residual amounts of propellant. A reduced particle size is obtaind from an increased distance to the patient as the propellant is then more completely evaporated. A reduced velocity and a reduced particle size are desirable in order to obtain a low deposition of substance on the mucous membranes of the oral cavity i.a. Thereby, a greater portion of the particles may follow the air inhaled into the pulmonary system and a better distribution is obtained into the small lumens of the lungs. Local side effects in the oral cavity may also be avoided as they are dependent on a high local concentration of drug substance.

Inhalation of drugs directly from the mouthpiece of a pressurized container requires a coordination between release of the dosage from the container and inspiration by the patient. Some patients have difficulties in performing such coordination.

It has been proposed to provide a pressurized aerosol container with a cylindrical or pear shaped inhalation tube (Moren, F; Int. J. Pharm. 1 (1978) 205-212). Such inhalation tubes may be used to avoid to some extent problems referred to above. However, to be an effective aid to the patient in need of inhalation therapy an inhalation device must be easy to put into operation. Devices in which parts must be assembled before use should be avoided in view of the acute conditions, e.g. asthmatic conditions under which some patients must take their medication. While providing a sufficient space for retardation of the drug particles and for evaporation of the propellant, the inhalation device must be sufficiently small to be carried with the patient. Further the interior of an inhalation device must be protected from contamination with dust. The object of the present invention is to provide an inhalation device fulfilling these requirements.

DISCLOSURE OF INVENTION

The present invention provides an aerosol inhalation device comprising an elongated chamber, provided at one end with means for connection thereof to an aerosol dispenser and having an outlet opening at the opposite end which opening is arranged to be brought to the mouth of a patient, said device being characterized in comprising at least two chamber parts each having a substantially rectangular cross section, of which an outer chamber part comprises the outlet opening and is telescopically displaceable over an inner chamber part, which at its outer end is provided with a flexible tongue which on telescoping the device together will close the outlet opening.

According to a preferred embodiment of the invention the portion of the outer chamber part comprising the outlet opening is shaped as a curved end wall along the inside of which the tongue of the inner part is arranged to run. With this embodiment of the invention it is further possible to design the device in such manner that the outlet opening may be tightly connected to the patient's mouth without requiring the patient's lips to be closed around a projecting mouthpiece as being required in prior art inhalation tubes. A further advantage of the device of the invention is that it may be made up of two parts only.

The invention is further described with reference to the enclosed drawings, of which FIG. 1 is a longitudinal sectional view of an aerosol inhalation device according to a preferred embodiment of the invention, connected to an aerosol dispenser, FIG. 2 is a cross sectional view along the line 2—2 of FIG. 1, FIG. 3 is a perspective view of the inhalation device shown in FIG. 1 as viewed from above, and FIG. 4 is a perspective view of said device viewed from below.

In the drawings 1 represents an outer chamber part having a portion 2 with a rectangular cross section and having a curved wall 3 with an outlet opening 4 at the front end thereof. The outer chamber part is telescopically displaceable over an inner chamber part 5 having such rectangular cross section as to fit within the outer chamber part and being provided at its rear end with an inwardly oriented sleeve 6 for connection of the inhalation device to a known aerosol dispenser 7 comprising a pressurized container 8 with a metering valve and a spray orifice 9. A flexible tongue 10 is projecting from one of the front edges of the inner chamber part 5, the flexible tongue being integral with said chamber part, the tongue being guided along the bottom of the outer chamber part 1 by guiding means 11 arranged at the side walls thereof. On sliding the two chamber parts together the free end of the tongue 10 will run along the inside of the curved wall 3, thereby closing the opening 4. The device may be held in a closed (storage) position by means of a locking edge 12 on the outside of the inner chamber part fitting with edges 13 on the inside of the outer part. In the open (operating) position the edge 12 will fit with corresponding edges 14. In FIG. 1 and 2 the device is shown in an intermediary position between the storage position and the operating position. To further secure against pulling the parts 1 and 5 apart the tongue 10 may be provided with shoulders near the front end thereof engaging in the operating condition of the device with openings 15 in the outer chamber part. At the rear end the device is provided with air inlet openings 16.

The device of the invention may be carried by the patient in the closed (storage) position assembled with an aerosol dispenser 7 comprising a pressurized container 8. The device may then easily be put into operating condition by pulling out the outer chamber part, whereafter the outlet opening is brought to the patient's mouth, an aerosol dose is released and inhaled through the device. In the known aerosol dispenser shown the dose is released by pressing down the pressurized container.

Figure 1:
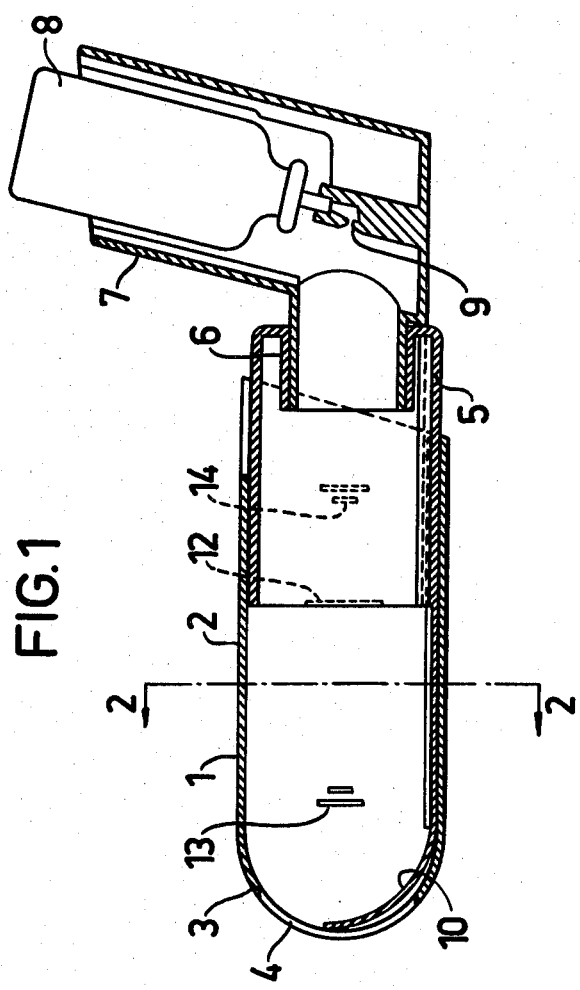
Figure 2:
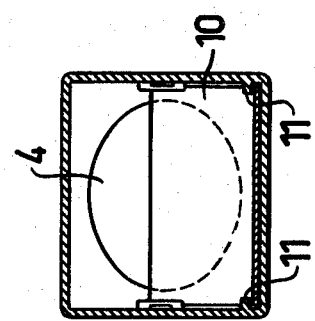
Figure 3:
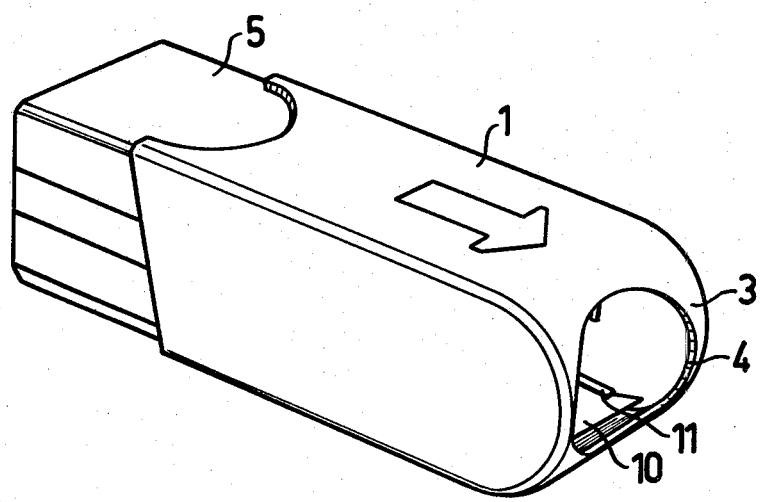
Figure 4:
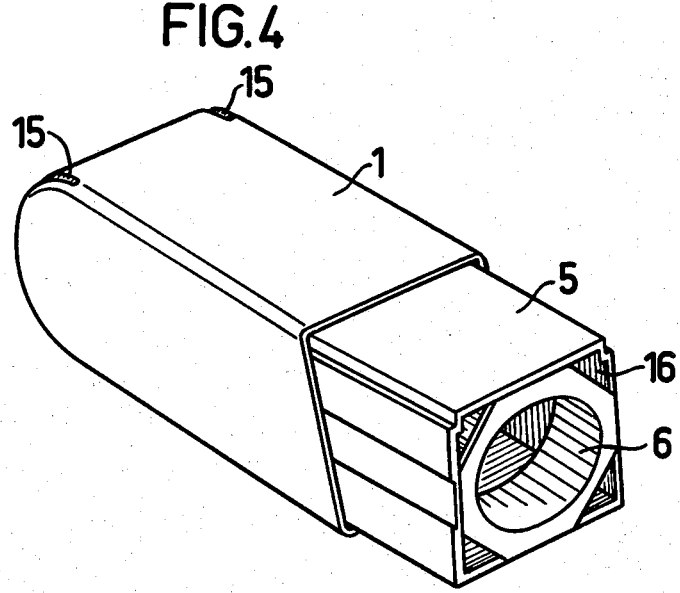

The device of the invention may be modified within the scope of the appended claims, thus the device may be designed to be connected to an aerosol dispenser different from that shown in FIGS. 1 and 2. The flexible tongue may be projecting from another front edge of the inner chamber part.

The length of the inhalation device in the operating position must be more than 5 cm and is suitably 10-20 cm measured from the orifice of the mouthpiece. The device is preferably made of plastic material e.g. polyethylene by injection moulding by the separate parts thereof.

BEST MODE OF CARRYING OUT THE INVENTION

The best mode of carrying out the invention known at present is the embodiment shown by the drawings and described with reference thereto, the length of the device in operating position being about 13 cm and the device being made of polyethylene.

We claim:

1. An aerosol inhalation device comprising an elongated chamber, provided at one end with means for connection thereof to an aerosol dispenser and having an outlet opening at the opposite end which opening is arranged to be brought to the mouth of a patient, characterized in comprising an outer chamber part and an inner chamber part each having a substantially rectangular cross section, said outer chamber part comprises the outlet opening and is telescopically displaceable over said inner chamber part, said inner chamber part at its outer end being provided with a flexible tongue, which on telescoping said chamber parts together will guide close said outer chamber part including guide means said flexible tongue to said outlet opening.

2. An aerosol inhalation device according to claim 1, characterized in that said guide means comprises the portion of the outer chamber part about the outlet opening being shaped as a curved end wall along the inside of which the tongue of the inner part is arranged to run.

* * * * *

UNITED STATES PATENT AND TRADEMARK OFFICE
CERTIFICATE OF CORRECTION

PATENT NO. : 4,292,966
DATED : Oct. 6, 1981
INVENTOR(S) : Monö et al.

It is certified that error appears in the above—identified patent and that said Letters Patent is hereby corrected as shown below:

Col. 4, line 14, after "tongue," insert --said outer chamber part including guide means--; and Col. 4, delete lines 16 and 17 and substitute therefor --guide said flexible tongue to close said outlet opening.--.

Signed and Sealed this

Second Day of February 1982

[SEAL]

Attest:

GERALD J. MOSSINGHOFF

Attesting Officer — Commissioner of Patents and Trademarks